United States Patent
Gueller et al.

(10) Patent No.: US 7,635,326 B2
(45) Date of Patent: *Dec. 22, 2009

(54) DEVICE COMPRISING A TOOL HOLDER AND A REMOVABLY ATTACHABLE TOOL

(75) Inventors: Rolf Gueller, Herznach (CH); Josef Schröer, Muttenz (CH); Paul Frank, Ennetbürgen (CH); Franz Metzger, Basel (CH); Christoph Bachmann, Lausen (DE); Gerhard Klokow, Rheinfelden (DE); Stefan Eichin, Zell i. W. (DE)

(73) Assignee: Chemspeed Technologies AG, Augst (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/931,927

(22) Filed: Oct. 31, 2007

(65) Prior Publication Data

US 2008/0050277 A1 Feb. 28, 2008

Related U.S. Application Data

(62) Division of application No. 10/381,403, filed on Mar. 24, 2003, now Pat. No. 7,513,857.

(30) Foreign Application Priority Data

Oct. 6, 2000 (CH) .................................. 1979/00
Oct. 4, 2001 (WO) .................. PCT/CH01/00598

(51) Int. Cl.
*B23Q 3/155* (2006.01)

(52) U.S. Cl. ............................. 483/16; 483/2; 483/901; 422/100; 422/81

(58) Field of Classification Search ................. 483/901, 483/16, 13, 2, 10, 12, 58–59; 901/30, 41, 901/43, 48, 49; 222/77, 58; 221/289; 279/128, 279/900; 422/63, 65, 81, 100; 436/47, 54, 436/180

See application file for complete search history.

(56) References Cited

U.S. PATENT DOCUMENTS 5,660,792 A * 8/1997 Koike .......................... 422/63

FOREIGN PATENT DOCUMENTS

| JP | 05-220691 A | * | 8/1993 |
| JP | 11-014630 A | * | 1/1999 |

OTHER PUBLICATIONS

Machine Translation of JP-05-220691-A.*

(Continued)

*Primary Examiner*—Erica E Cadugan
(74) *Attorney, Agent, or Firm*—Husch Blackwell Sanders Welsh & Katz

(57) ABSTRACT

The inventive device comprises a tool holder (1), which can be displaced in an x-direction, in a y-direction that is perpendicular thereto, and in a z-direction that is perpendicular to both the x-direction and the y-direction, and which can rotate about the z-direction. A solid matter dosing head (350), provided as a tool, is automatically attached in a removable manner to the tool holder (1) by means of a permanent magnet (351). The tool can be easily exchanged for another tool due to this automatic removable attachment of said tool to the tool holder (1) involving the use of a permanent magnet (351).

11 Claims, 12 Drawing Sheets

OTHER PUBLICATIONS

Machine Translation of JP-11014630-A.*
Powdernium AD: Operating and Maintenance Instruction (2000) 12 pages.
Bohdan: Caco-2 Assay Workstation (www.bohdan.com/caco2.htm) Product Highlights and Capabilities (Sep. 19, 2000) 3 pages.
The AutoDose L1000 Powder Dispenser (www.scitec-automation.ch)/autodose.htm) (May 12, 2000) 1 page.
Quad-Z215: High throughput Liquid Handler and Injector with four independent probes (www.gilson.com/c250spec.htm) (Aug. 8, 2000) 7 pages.
Genesis—Robotic Sample Processor (www.tecan.com/tec_rsp.htm) (Sep. 19, 2000) 4 pages.
Tecan MiniPrep Series Robotic Sample Processors 2 pages.
Powdernium 1.3x User Manual (2000) 18 pages.

* cited by examiner

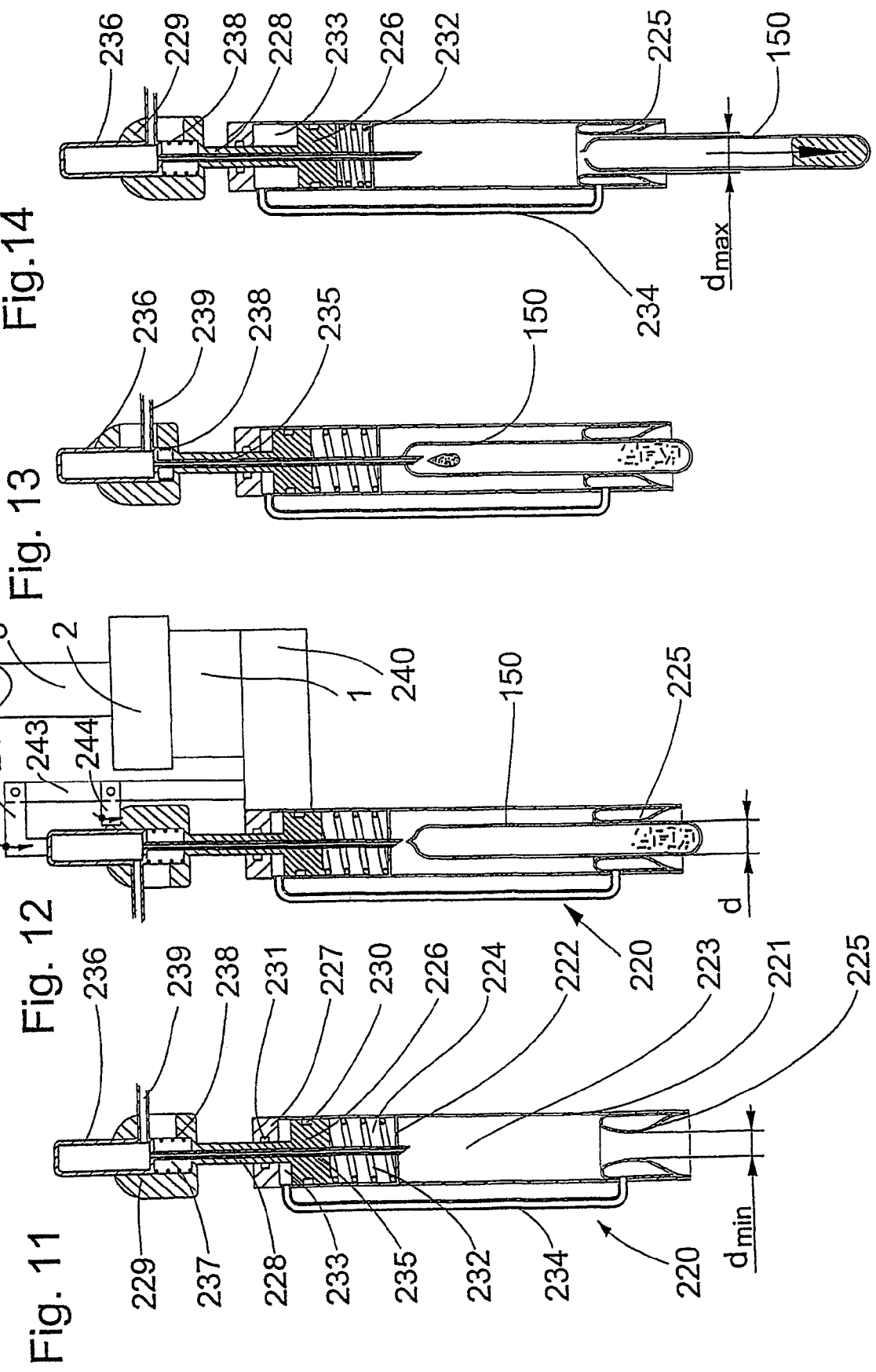

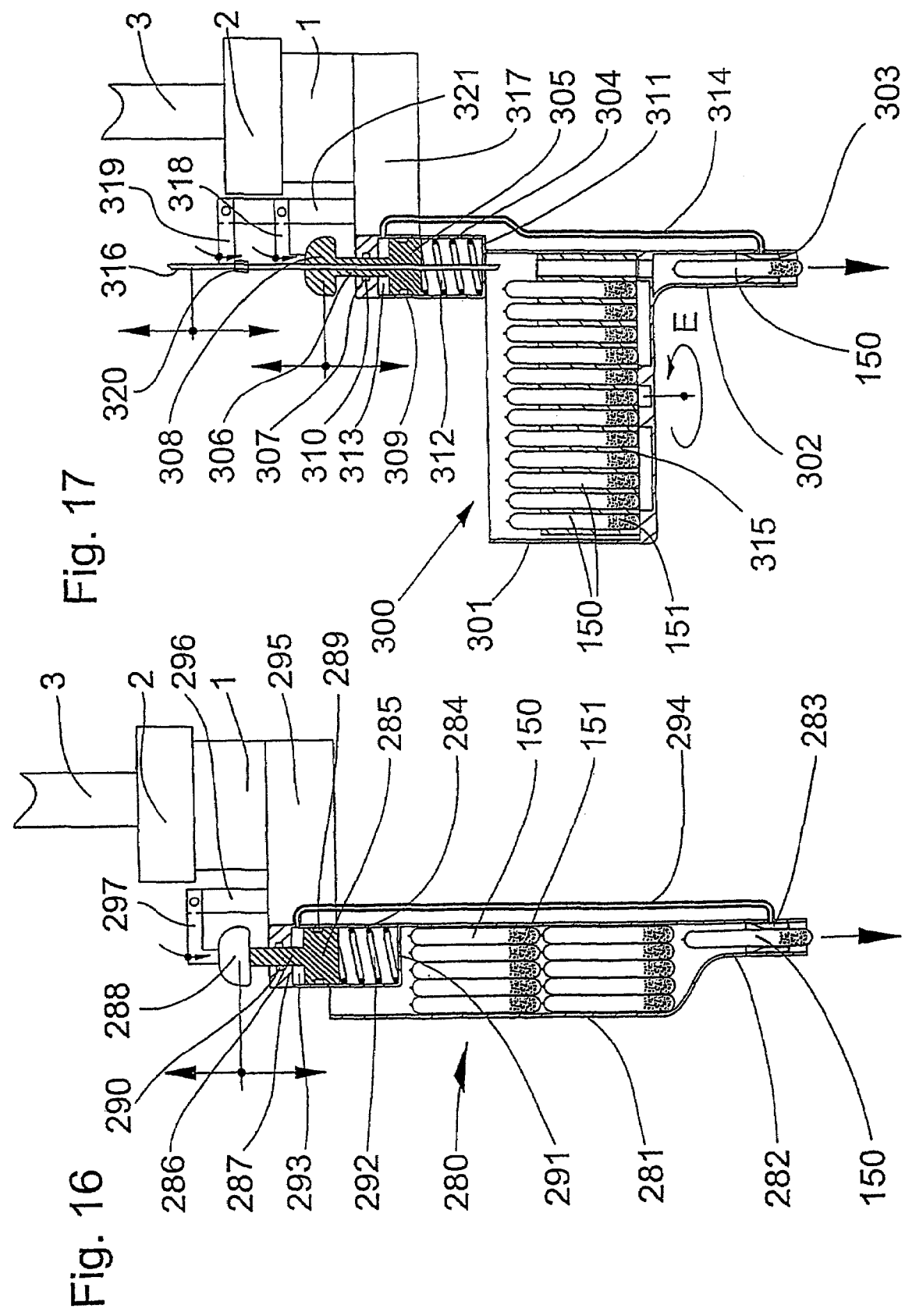

DEVICE COMPRISING A TOOL HOLDER AND A REMOVABLY ATTACHABLE TOOL

CROSS-REFERENCE TO RELATED APPLICATIONS

This application is a divisional application of Ser. No. 10/381,403, filed Mar. 24, 2003, which is a 371 of PCT/CH01/00598, filed Oct. 4, 2001.

BACKGROUND OF THE INVENTION

The present invention relates to a device having a tool holder, which can be displaced in an x direction and a z direction which is perpendicular to the x direction, and a first tool in the form of a metering head, which can be removably secured to the tool holder.

Devices of this type are used, inter alia, for automatically metering substances into a plurality of reaction vessels or test tubes which are arranged, for example, next to one another.

In a device which is known as Caco-2 Assay produced by Mettler Toledo Bohdan, Greifensee, Switzerland, there are two tool holders with different tools. The tool holders can be displaced in a horizontal x direction, a horizontal y direction which is perpendicular to the x direction, and a vertical z direction which is perpendicular to the x and y directions, and in this way can serve reaction vessels arranged next to one another under the control of software. One of the tools is designed for metering liquid as a metering head in the form of a four-needle head with four parallel hollow needles which can be spread apart. The other tool is a gripper for handling substance plates which have a multiplicity of recesses for holding substance. To weigh matter which can be handled by the device, there is a balance, on which, by way of example, a corresponding substance plate or a test tube is placed.

Although the two fixedly installed tools do make it possible to handle liquids and solids, they do not, for example, allow a solid to be metered directly into a reaction vessel. Moreover, there are two tool holders which have to be able to move independently of one another, in which context it must be ensured that they do not collide with one another. Finally, accurate weighing out of a defined quantity of substance is relatively complex.

SUMMARY OF THE INVENTION

In view of the drawbacks of the devices of the prior art which has been described above, the invention is based on the object of providing a device which allows a very wide range of forms of substances to be handled as simply as possible.

This object is achieved by the device according to the invention as defined in the independent patent claims. Preferred variant embodiments will emerge from the dependent patent claims.

The essence of the invention consists in the following: a device comprises a tool holder, which can be displaced in an x direction and a z direction which is perpendicular to the x direction, and a first tool in the form of a metering head, which can be removably secured to the tool holder. It comprises at least one further, other tool, which can be removably secured to the tool holder as an alternative to the first tool and which has at least one part which can move actively and independently of the movement of the tool holder, it being possible for the securing and removal of in each case one of the tools to be carried out automatically.

In the present context, the terms automatic securing and removal of a tool is understood as meaning that the securing and removal are carried out not by hand but rather by the device itself, at most under the control of an operator.

The fact that the device comprises various tools with different functions which can automatically be secured to and removed from the tool holder as alternatives means that a very wide range of substances, solids, etc. can be handled without problems. Since there is in each case only one tool attached to the tool holder, there is no risk of different tool holders and tools getting in one another's way.

The fact that the further tool has at least one part which can move actively and independently of the movement of the tool holder results in better and additional use options compared to a mechanically passive tool or a tool whose movement is dependent on the tool holder.

In an advantageous exemplary embodiment, the metering head carries with it a storage container which contains all the substance which is to be metered. This eliminates the need for substance-feed hoses, etc. leading to the metering head or to the tool holder. This has the additional advantage that the metering head can move more freely, without being impeded by hoses, etc.

In a preferred exemplary embodiment, the tool holder can rotate about the z direction. This in particular allows the tool to rotate through, for example, 90.degree., i.e. allows, by way of example, a multi-needle head having a plurality of hollow needles arranged next to one another to be used to meter substances, which may differ according to the hollow needle used, to vessels belonging to a matrix in rows, then allows the multi-needle head to be rotated through 90.degree and substances, which once again may differ according to the hollow needle used, to be metered to the vessels of the matrix in columns. It is thus possible for a different combination of substances to be metered to each vessel of the matrix in a simple way. Moreover, the rotation allows reaction vessels, starting-material bottles, etc. to be arranged over an area and not just on a straight line.

Preferably, the tool holder can additionally be displaced in a y direction, which is perpendicular to the x direction and the z direction. This enables reaction vessels, starting-material bottles, etc. to be arranged over a larger area.

In an advantageous variant embodiment, the tool is secured to the tool holder by means of magnets, in which case it is preferable, where there are two permanent magnets which attract one another, for one of the two permanent magnets to be arranged on the tool holder and the other of the two permanent magnets to be arranged on the tool, and for it to be possible for the action of the attraction between the two permanent magnets to be cancelled out by means of at least one electromagnet. Connecting tool and tool holder by means of magnets allows automatic securing of the tool to the tool holder, for example by the tool holder being guided over the tool and then lowered onto it or the tool holder being moved laterally onto the tool. Detaching the tool from the tool holder by activating the at least one electromagnet by means of current pulses also contributes to enabling the tool change to take place automatically.

In alternative advantageous variant embodiments, the tool is secured to the tool holder by screw connection, by means of a bayonet catch or by means of a clamping connection, etc. Although these methods of securing are normally more complex to implement, they are relatively simple to automate, in particular if the tool holder can be rotated about the z direction.

Preferably, one of the tools is a screw metering head, which comprises a screw which can rotate forward and backward about the z direction in a tube which is at least partially open at its lower end and which can be used to take up and dispense substance. A screw metering head of this type can be used for targeted removal of pulverulent or liquid substance from a storage vessel and also for targeted dispensing of this substance.

Advantageously, the lower open end of the tube can be closed off by a diaphragm provided with holes, and there is preferably a ram, which runs on the screw and presses substance through the diaphragm as the screw rotates when substance is being dispensed, arranged in the tube. The use of a diaphragm leads to more uniform dispensing of substance, since the substance is forced uniformly through the holes in the diaphragm. This in turn has the advantage that metering can be carried out more accurately.

Advantageously, one of the tools is a capsule-transporting head, by means of which a capsule can be picked up and released, preferably by suction. A tool of this type makes it possible to transport substances in capsules or similar containers.

Preferably, one of the tools is a matrix-capsule-transporting head, by means of which capsules which are arranged in the manner of a matrix can be picked up, preferably by suction, and the capsules can be released individually, together or in groups. The matrix-capsule-transporting head also makes it possible to transport substances in capsules, it being possible for a large number of capsules which are arranged in matrix form to be handled at the same time.

Advantageously, one of the tools is a capsule-handling head, by means of which at least one capsule can be picked up, which capsule can be opened in the tool, preferably by means of a hollow needle, and in which tool the contents of the capsule can preferably be mixed with another substance, in particular a solvent. The mixing can be effected, for example, by adding solvent to the capsule, sucking up substance and solvent from the capsule and returning the material which has been sucked up into the capsule. Alternatively, the hollow needle can also be used to suck substance out of the capsule and dispense it again at another location. The capsule-handling head according to the invention makes it possible to prepare even more successfully for chemical reactions outside a reaction vessel.

In a preferred variant embodiment, one of the tools is a matrix-capsule-handling head, by means of which a plurality of capsules which are arranged in the form of a matrix can be picked up, which capsules can be opened in the tool, preferably using hollow needles, and in which tool the contents of one capsule can preferably in each case be mixed with another substance, in particular a solvent. The mixing can be effected, for example, by adding solvent to the capsule, sucking up substance and solvent from the capsule and returning the material which has been sucked up into the capsule. Alternatively, the hollow needle can also be used to suck substance out of the capsule and dispense it again at another location. The matrix-capsule-handling head also makes it possible to handle substances in capsules and to prepare for chemical reactions, it being possible for a multiplicity of capsules which are arranged in the form of a matrix to be picked up and processed simultaneously.

In another preferred variant embodiment, one of the tools is a capsule-dispensing head, in which a multiplicity of capsules are stored and can be dispensed individually, together or in groups, it preferably being possible for the capsules to be opened in the capsule-dispensing head, and it even more preferably being possible for the contents of the capsules to be mixed with another substance, in particular a solvent, in the capsule-dispensing head. The capsule-dispensing head according to the invention makes it possible to prepare for chemical reactions largely outside a reaction vessel and means that the appropriate capsules or the contents thereof simply have to be added to the reaction vessel in order to carry out these chemical reactions.

Advantageously, one of the tools is a needle head with a hollow needle, a multi-needle head with a plurality of hollow needles, which can preferably be displaced individually in the z direction and/or the distance between which can preferably be adjusted, a gripper, a lid opener, or a solids-metering head. Tools of this type additionally increase the possible uses of the device according to the invention.

Advantageously, one of the tools is a combination head having at least two identical or different tool parts, one of the tool parts preferably being a needle head, multi-needle head, gripper, lid opener, capsule-transporting head, matrix-capsule-transporting head, capsule-handling head, matrix-capsule-handling head, capsule-dispensing head, screw metering head or solids-metering head. This allows a plurality of method steps to be carried out in succession or simultaneously using a single tool.

In a preferred exemplary embodiment, a balance, which can be used to weigh substance or capsules which has/have been taken up or dispensed by the tool, is arranged on the tool or on the tool holder.

The fact that a balance is arranged directly on the tool or on the tool holder makes it possible to weigh a substance, a substance capsule or another object which has been taken up or dispensed without the substance, the substance capsule or the other object or the tool for this purpose having to be placed onto a separate balance. Weighing in situ means that the material to be weighed does not have to be displaced, yet it is not necessary for a balance to be arranged at each working position, e.g. under each reaction vessel. This significantly simplifies the weighing operation.

A method for weighing out a desired quantity of substance using a device having a tool holder, which can be displaced in an x direction and a z direction which is perpendicular to the x direction, and a tool in the form of a metering head, which is secured to the tool holder, and a balance arranged on the tool or on the tool holder, by means of which substance which has been taken up by the tool can be weighed, is characterized by the steps that a) substance is taken up by the tool;

b) the substance is weighed;

c) the difference between the weighed value obtained and the desired set value is calculated; and d) if the difference lies outside the range of a desired level of accuracy, the tool is used to discharge substance or take up additional substance depending on this difference;

steps b) to d) being repeated until the difference is equal to zero within the range of a desired level of accuracy.

A similar method for selecting a capsule with a desired quantity of substance using a device having a tool holder, which can be displaced in an x direction and a z direction which is perpendicular to the x direction, and a tool in the form of a metering head, which is secured to the tool holder, and a balance which is arranged on the tool or on the tool holder and can be used to weigh capsules which have been picked up by the tool, is characterized by the steps that a) the tool is used to pick up a capsule containing substance;

b) the capsule with substance is weighed;

c) the difference between the weighed value obtained and the desired set value is calculated; and d) if the difference lies outside the range of a desired level of accuracy, the capsule is released again from the tool and a new capsule containing substance is picked up;

steps b) to d) being repeated until the difference is equal to zero within the range of a desired level of accuracy.

These two weighing methods which operate in accordance with the test principle make it easy to weigh out a desired quantity of substance or a desired object with the desired level of accuracy.

Advantageously, the device according to the invention has a camera, which is preferably arranged on the tool holder and which can be used to film an area below the tool holder, as well as a control computer having an image-processing unit, which evaluates images which have been filmed by the camera, it preferably being possible for the displacement of the tool holder and, the selection, securing or release of one of the tools to be controlled on the basis of the evaluation result.

In an advantageous alternative variant, the device according to the invention has an infrared analysis unit, which is preferably arranged on the tool holder and has an infrared transmitter, by means of which infrared waves can be radiated into an area below the tool holder, and an infrared sensor, which can be used to measure reflected infrared waves, as well as a control computer having a measured-value-processing unit, which evaluates the reflected infrared waves measured by the infrared sensor, it preferably being possible for the displacement of the tool holder and, the selection, securing or release of one of the tools to be controlled on the basis of the evaluation result. The precise way in which an infrared analysis unit of this type functions is described, for example, in U.S. Pat. No. 6,031,233, which is hereby specifically incorporated by reference in the present description.

The camera or the infrared analysis unit, together with the control computer, allows the device to operate completely automatically without an operator having to evaluate the substance or capsule to be handled and then actively control the displacement of the tool holder and/or the selection, securing or release of one of the tools.

Further advantageous tools comprise, for example, a sensor, e.g. a pH sensor, a bar code reader, etc.

In an advantageous variant embodiment, the device according to the invention comprises a further tool holder for attachment of a further tool which can be displaced in an x direction and in a z direction which is perpendicular to the x direction, it preferably additionally being able to rotate about the z direction and/or to be displaced in a y direction which is perpendicular to the x direction and to the z direction. The second tool holder may be designed and controlled in the same way as the first. With two or even more tool holders with tools attached to them, it is possible to multiply the speed of the device; at the control, it must be ensured that the various tool holders and tools do not impede one another.

BRIEF DESCRIPTION OF THE DRAWINGS

The devices according to the invention are described in more detail below with reference to the appended drawings and on the basis of exemplary embodiments. In the drawings:

FIG. 11 shows a section view of a tool in the form of a capsule-handling head with hollow needle;

FIG. 12 shows the capsule-handling head from FIG. 11 on the tool holder from FIG. 1 with a closed capsule which has been picked up;

FIG. 13 shows the capsule-handling head with a capsule which has been picked up as shown in FIG. 12 during the addition of solvent after the capsule has been punctured by the hollow needle;

FIG. 14 shows the capsule-handling head with punctured capsule as shown in FIG. 13 when the capsule, which now contains dissolved substance, is being dispensed;

FIG. 16 shows a sectional view of a tool in the form of a first exemplary embodiment of a capsule-dispensing head having a multiplicity of stored capsules at the tool holder shown in FIG. 1;

FIG. 17 shows a sectional view of a tool in the form of a second exemplary embodiment of a capsule-dispensing head having a multiplicity of stored capsules which can be opened in the capsule-dispensing head, at the tool holder shown in FIG. 1;

DETAILED DESCRIPTION OF THE INVENTION

FIG. 1

Figure 1:
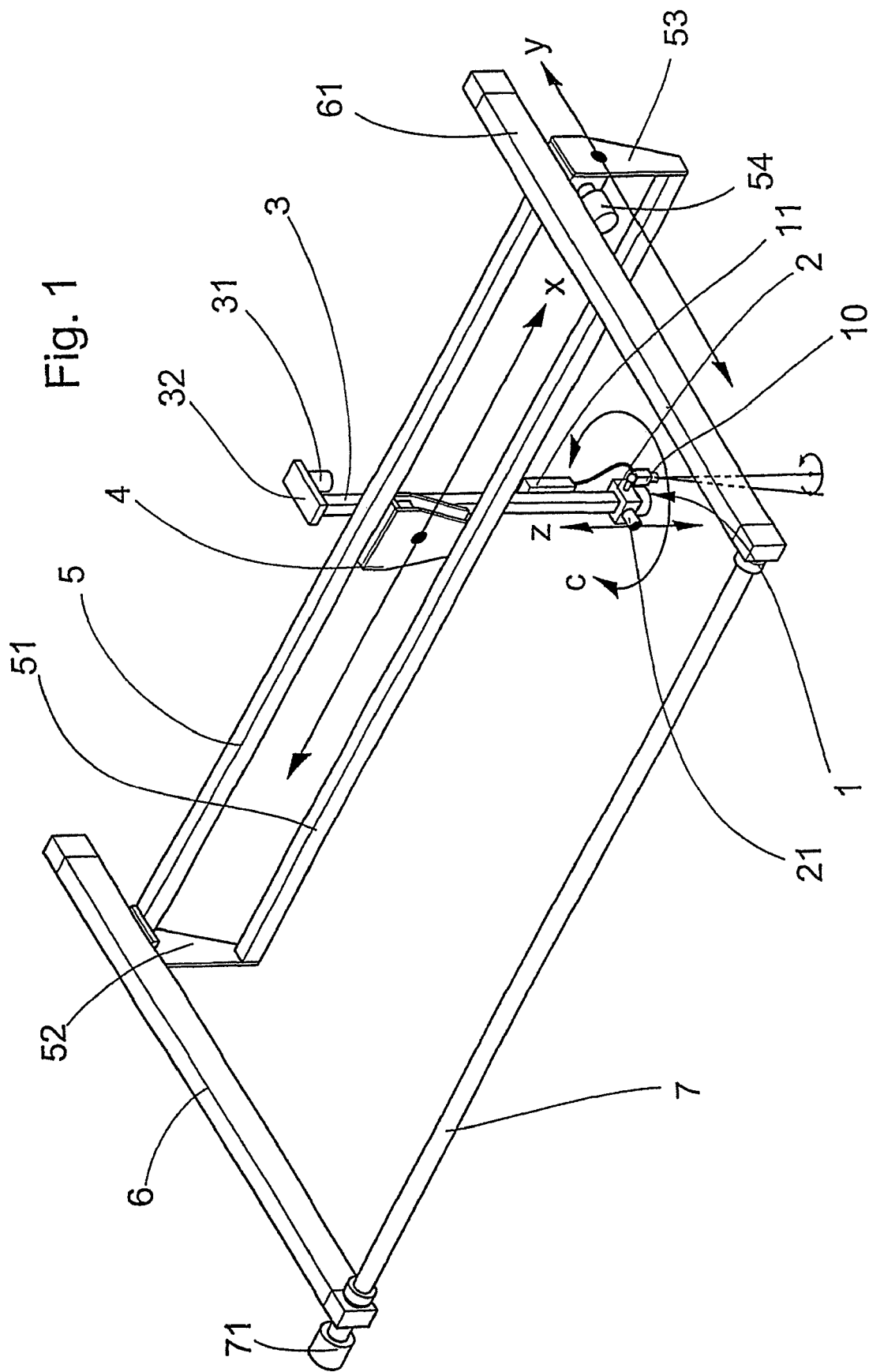
FIG. 1 shows a tool holder which can be displaced in all three spatial directions x, y and z on a linear axis system and can rotate about the z direction.

A linear axis system for holding and displacing a tool holder 1 comprises two guide rails 6, 61, which run parallel to one another in the y direction and are anchored in a fixed position in a manner which is not illustrated. The first ends of the two guide rails 6, 61 are connected by a rotary rod 7, which can be rotated by means of a stepper motor 71. An upper running rail 5 is secured to the two guide rails 6, 61 in such a manner that it can be displaced in the y direction. The upper running rail 5 is fixedly connected to a lower running rail 51 by means of two end plates 52, 53. As a result of the rotary rod 7 being rotated by means of the stepper motor 71, in each case one toothed belt in the interior of the guide rails 6, 61 is driven, causing the running rails 5, 51 to be displaced in the y direction. In the present context, the term displacement in the y direction is to be understood as meaning both a displacement in the +y direction and in the −y direction (the opposite direction).

Carriage 4 is secured to the two running rails 5, 51 in such a manner that it can be moved in the x direction. In the present context, the term movement in the x direction is once again to be understood as meaning both a movement in the +x direction and in the −x direction (the opposite direction). The carriage 4 is driven by a stepper motor 54 via a toothed belt arranged in the hollow upper guide rail 5.

A tool rod 3 is secured to the carriage 4 in such a manner that it can move in the z direction. In the present context, the term movement in the z direction is once again to be understood as meaning both a movement in the +z direction and in the −z direction (the opposite direction). In order for the tool rod 3 to be displaced, a stepper motor 31 is attached to it via a hollow plate 32, and a toothed belt is arranged in the hollow plate 32 and the tool rod 3.

At the lower end of the tool rod 3 there is a rotary drive 2, to which the tool holder 1 is secured. The tool holder 1 can be rotated both ways about the z direction, as indicated by the arrow c, with the aid of a rotary motor 21. In order to secure and release a tool, the tool holder 1 substantially consists of a permanent magnet, in which an electromagnet is arranged.

A camera 10, which is directed downward in the z direction and can be used to film an area below the tool holder 1, is attached to the tool holder 1. The images which are filmed by the camera 10 are transmitted via a data line to an image-processing unit of a control computer 11, which evaluates these images. The control computer 11 can then control the displacement of the tool holder 1 in the x, y, z and c directions by means of the motors 54, 71, 31 and 21 and the selection, securing or release of a tool on the basis of the evaluation results.

The following consideration applies to the whole of the remainder of the description. If a figure includes reference symbols which are provided for the purpose of clarity of the drawing but these reference symbols are not mentioned in the immediately associated text of the description, or vice versa, reference is made to the corresponding explanations given in preceding descriptions of figures.

FIG. 2

In this case, a needle head 100 is removably secured as the tool to the tool holder 1 by means of a permanent magnet 101. The permanent magnet 101 of the needle head 100 and the permanent magnet of the tool holder 1 attract one another, so that when the needle head 100 is removed it can be secured to the tool holder 1 by placing the tool holder 1 on it, an operation which can be performed automatically, i.e. the needle head 100 does not have to be attached to the tool holder 1 manually. The needle head 100 is detached from the tool holder 1 by means of the electromagnet which is arranged in the tool holder 1, cannot be seen and, when it receives a current pulse, cancels out the action of the attraction between the permanent magnet 101 of the needle head 100 and the permanent magnet of the tool holder 1.

A linear drive 103 is attached to the permanent magnet 101 via a plate 102. A hollow needle 105 is secured to the outer cylinder of the linear drive 103 by means of two holding parts 104, which are provided with continuous receiving holes for the hollow needle 105. With the aid of the linear drive 103, the hollow needle 105 can be displaced in the z direction.

A hollow needle 105 of this type can be used, for example, to meter or remove liquid substances into or from reaction vessels. In particular, for this purpose a suction and/or blowing means can be connected to the top end of the hollow needle 105.

Figure 3:
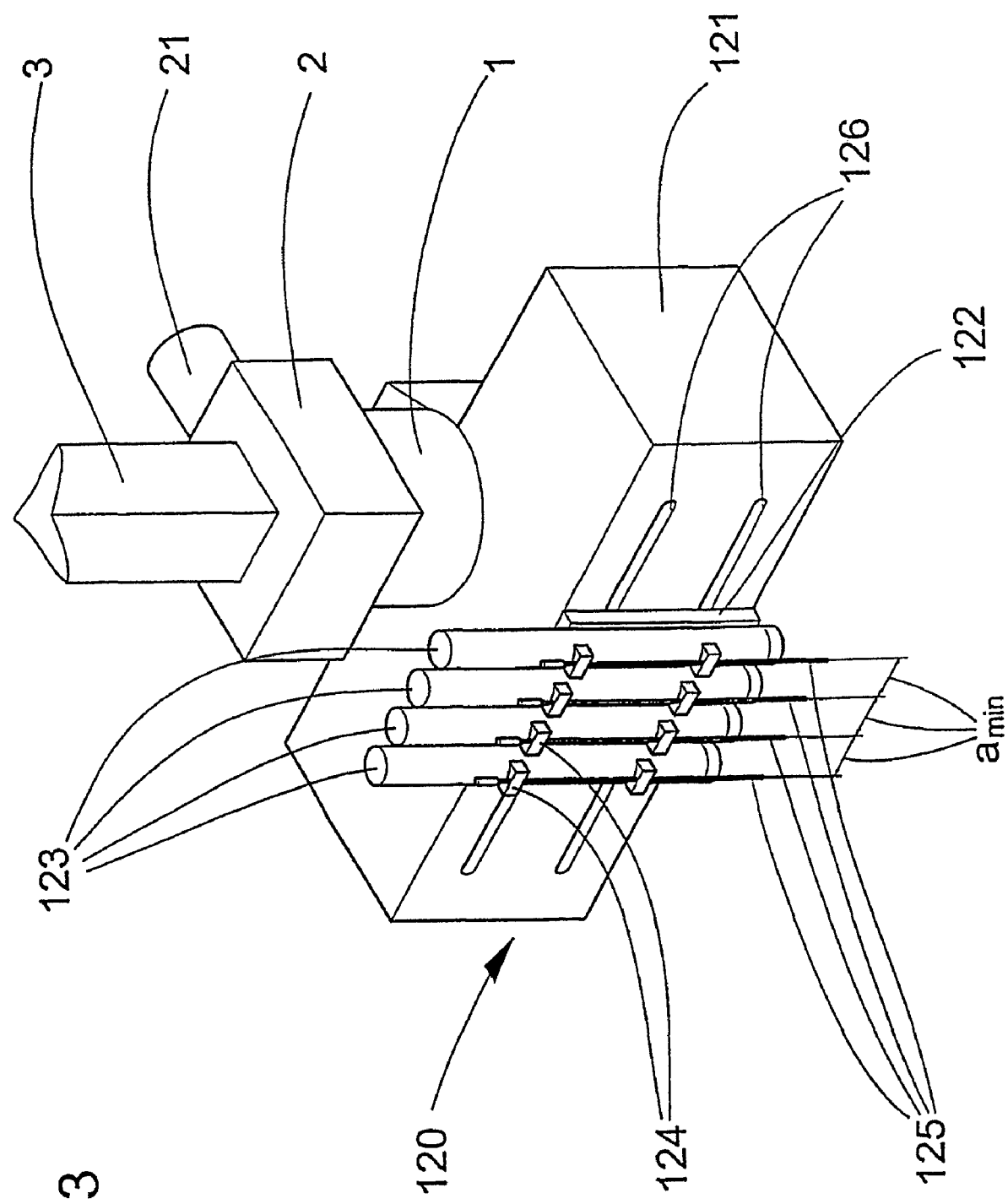
FIG. 3 shows the tool holder from FIG. 1, having a needle head with four hollow needles which can be displaced with respect to one another as tool, the four hollow needles being at a minimum distance from one another.
Figure 4:
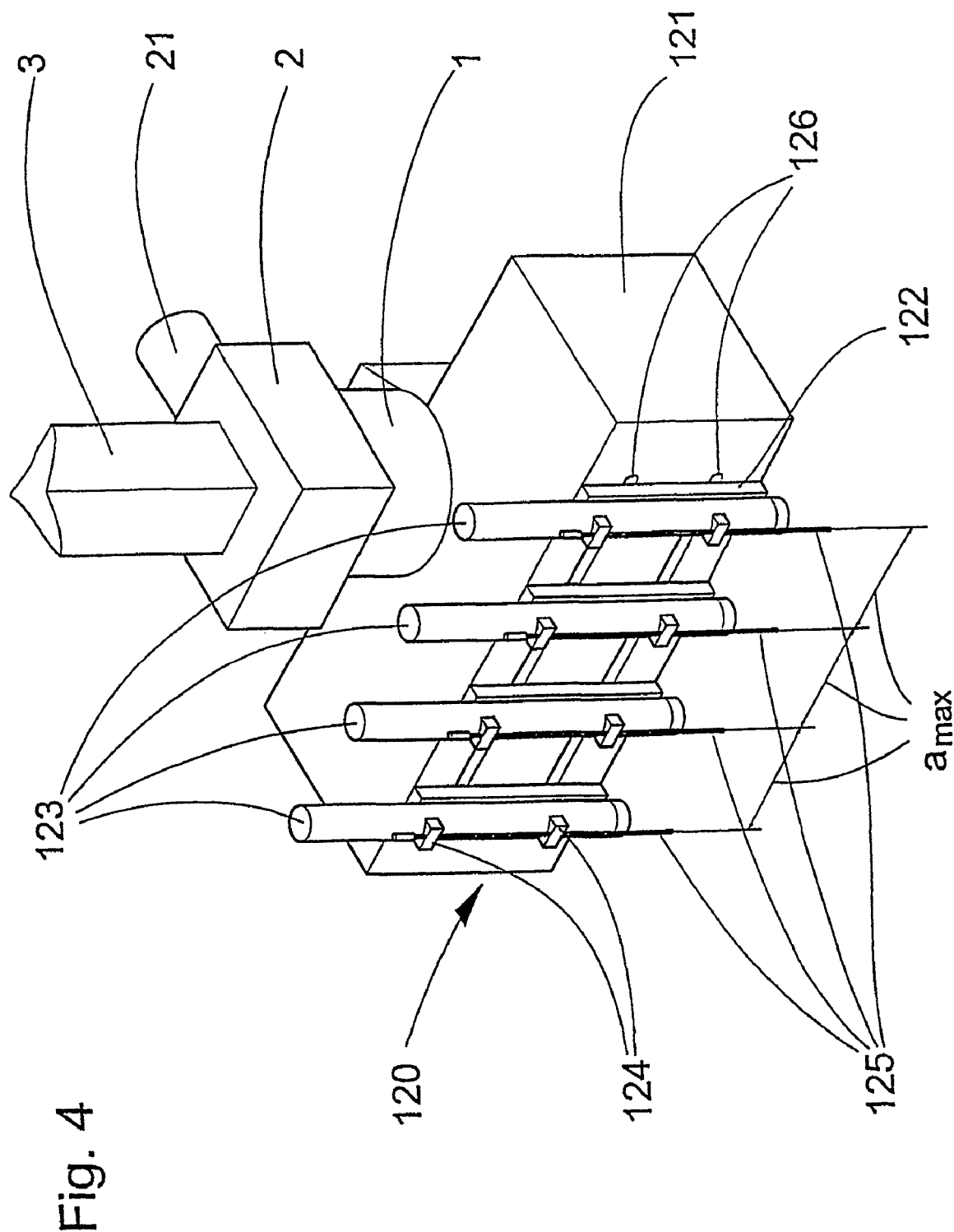
FIG. 4 shows the tool holder with needle head from FIG. 3, with the four hollow needles at a maximum distance from one another.
Figure 5:
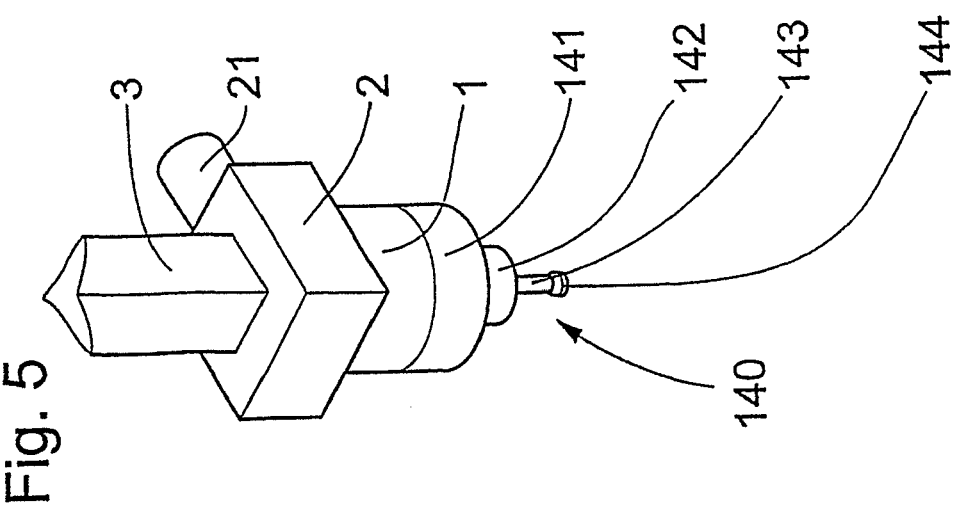
FIG. 5 shows the tool holder from FIG. 1 with a capsule-transporting head as tool.

FIGS. 3 and 4

Figure 2:
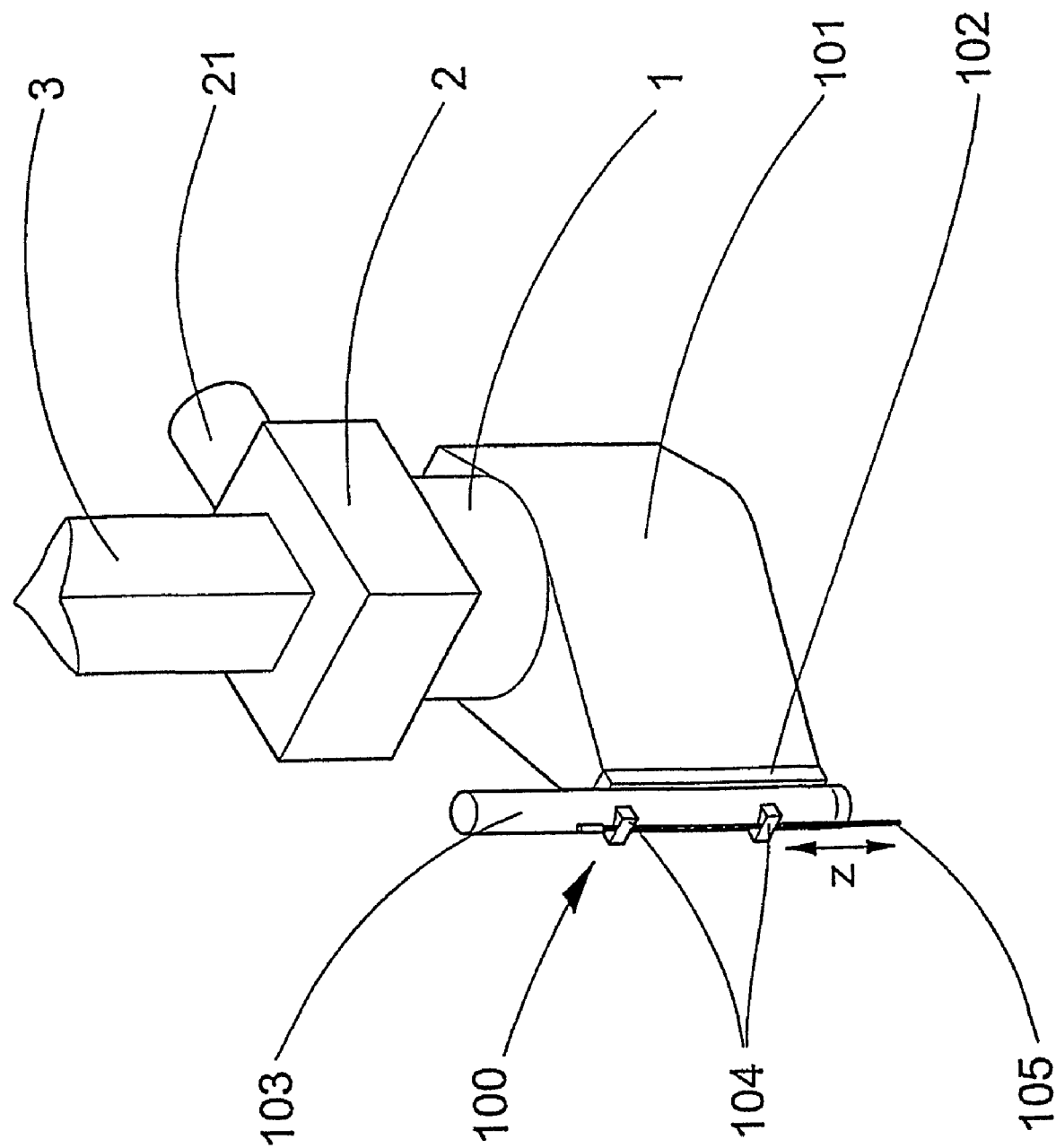
FIG. 2 shows the tool holder from FIG. 1, having a needle head with a hollow needle as tool.

The tool is in this case formed by a needle head 120 with four hollow needles 125, which can be individually displaced in the z direction and the distance between which can be adjusted from a minimum distance $a_{min}$ to a maximum distance $a_{max}$, the distance between each pair of adjacent hollow needles 125 always being identical. To this end, the hollow needles 125 are each secured to the outer cylinder of a linear drive 123 by means of two holding parts 124 which are provided with continuous hollow-needle-receiving holes. The linear drives 123 which can be used to displace the hollow needles 125 individually in the z direction are for their part in each case attached to an associated plate 122. The four plates 122 are arranged movably in two grooves in a permanent magnet 121, the drive for this purpose being effected by means of two spindles which are driven by a motor and are located inside the permanent magnet 121. The needle head 120, as described in connection with FIG. 2, is connected to the tool holder 1 via the permanent magnet 121. Once again, the needle head 120 is detached from the tool holder 1 by means of the electromagnet (not visible) arranged in the tool holder 1.

A needle head 120 of this type can be used, for example, to successively meter different liquids to a reaction vessel or to meter liquid to or remove liquid from a plurality of reaction vessels simultaneously. In particular suction and/or blowing devices can be connected to the top end of the hollow needles 125 for this purpose.

FIG. 5 to 7

The tool is in this case formed by a capsule-transporting head 140, by means of which a tightly closed capsule 150, which is in the form of a small tube and contains a pulverulent substance 151, can be picked up by suction. The capsule-transporting head 140 comprises a permanent magnet 141, by means of which, as described in a corresponding way in connection with FIG. 2, it is connected to the tool holder 1. It can be released by means of the electromagnet arranged in the tool holder 1. A suction tube 143 having a capsule-holding end piece 144 is attached to the permanent magnet 141 via an intermediate part 142. A reduced pressure can be generated in the suction tube 143 by means of a conventional suction means (not shown).

Figure 6:
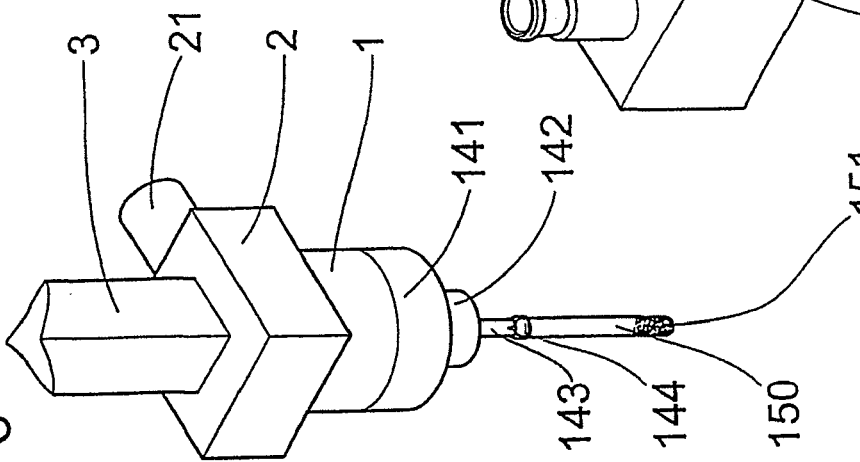
FIG. 6 shows the capsule-transporting head from FIG. 5 when it is holding a capsule.
Figure 7:
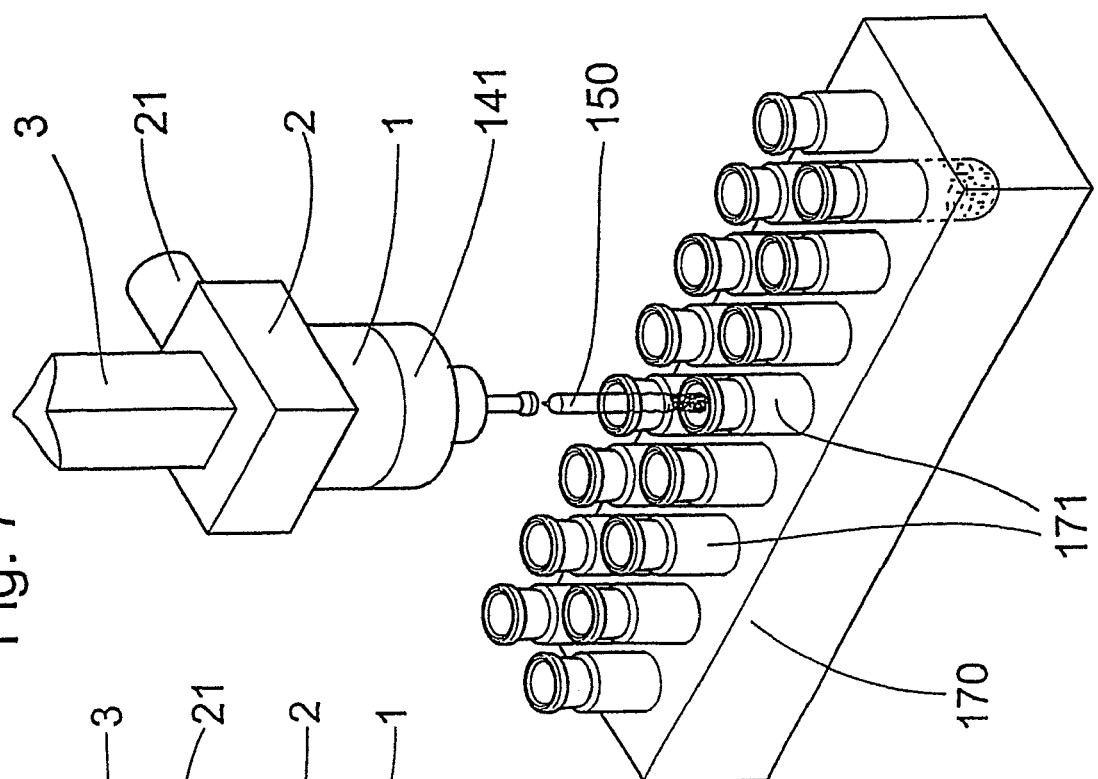
FIG. 7 shows the capsule-transporting head from FIG. 5 when a capsule is being placed in a reaction vessel arranged in a matrix.
Figure 8:
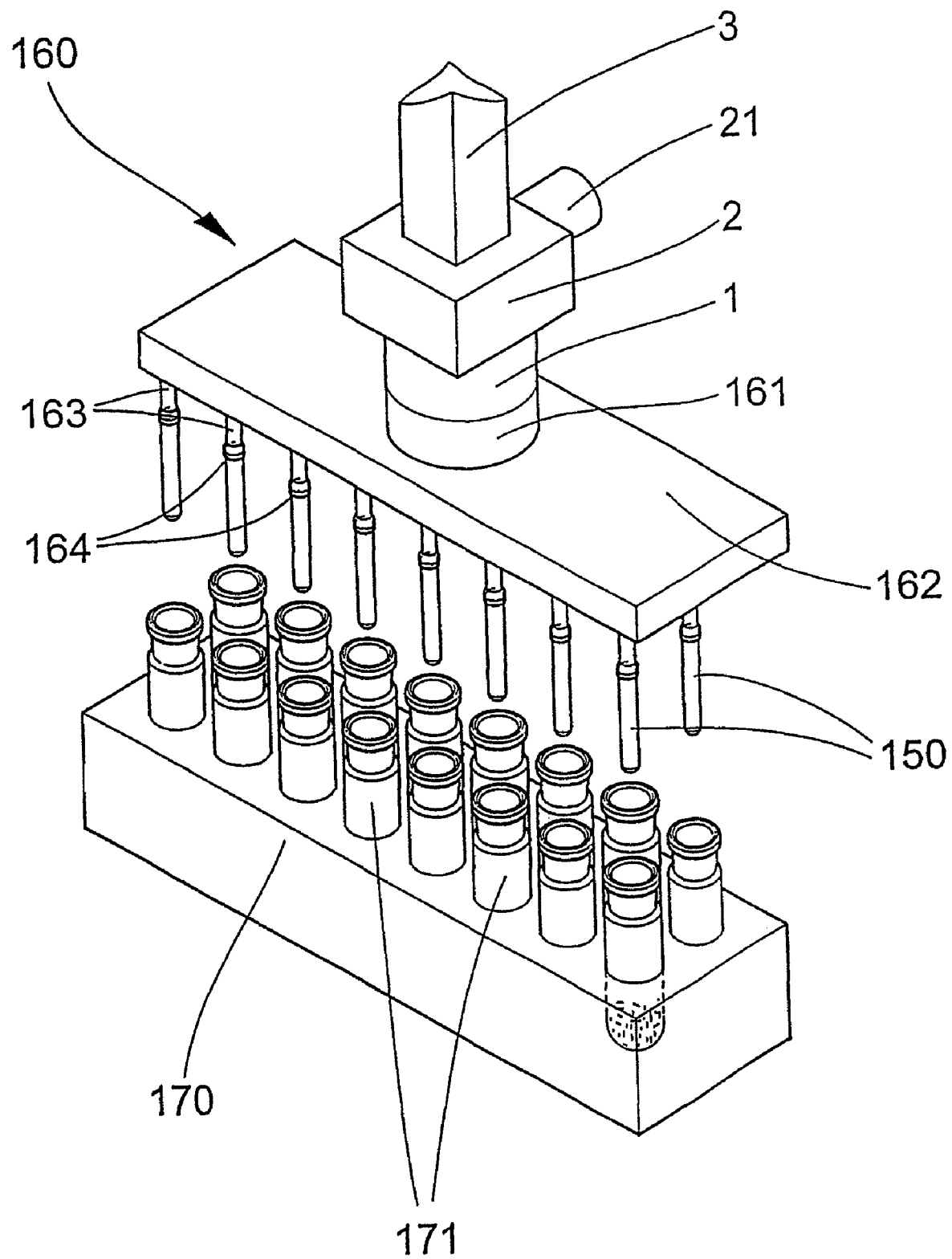
FIG. 8 shows the tool holder from FIG. 1 with a matrix-capsule-transporting head as tool.
Figure 10:
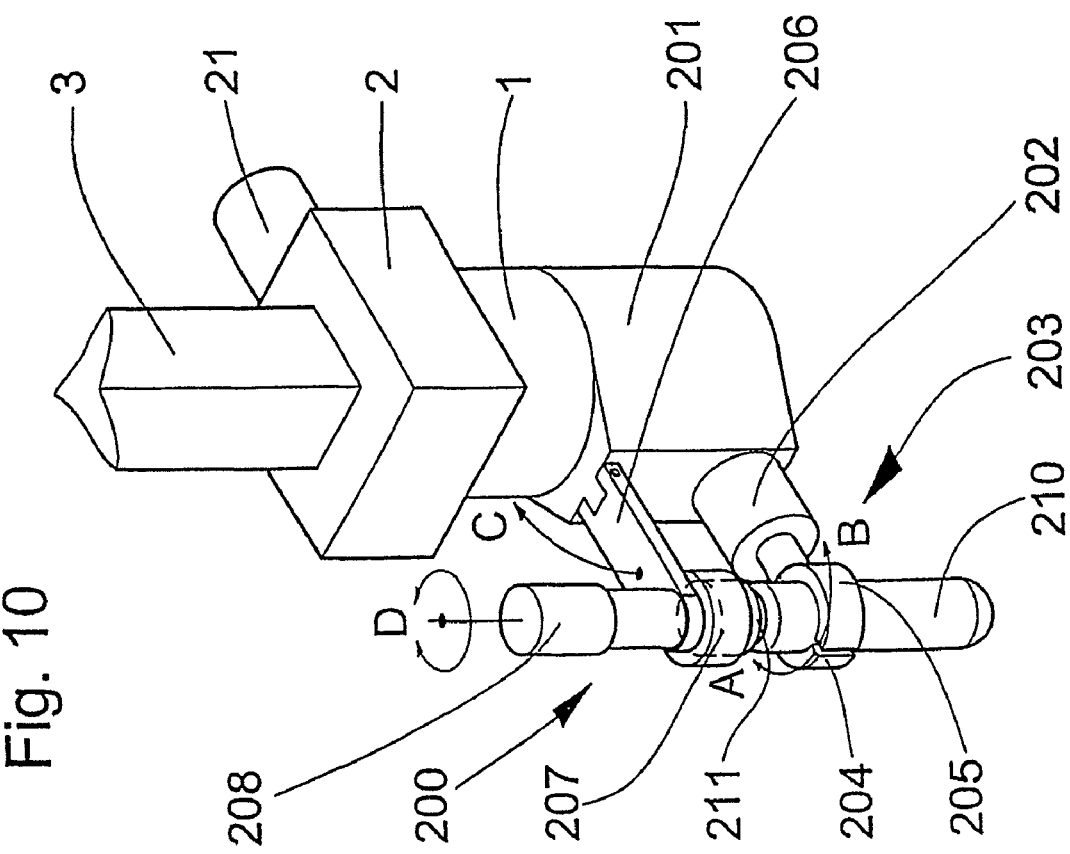
FIG. 10 shows the tool holder from FIG. 1 with a lid opener as tool.
Figure 9:
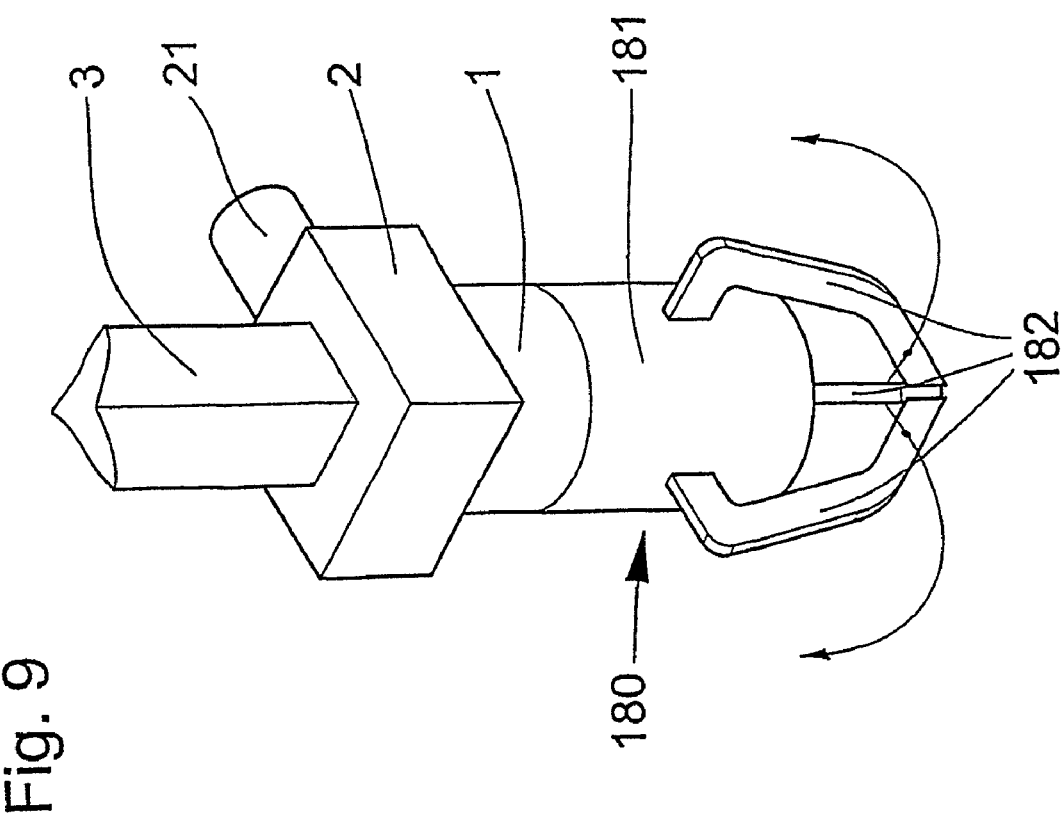
FIG. 9 shows the tool holder from FIG. 1, with a gripper as tool.
Figure 15:
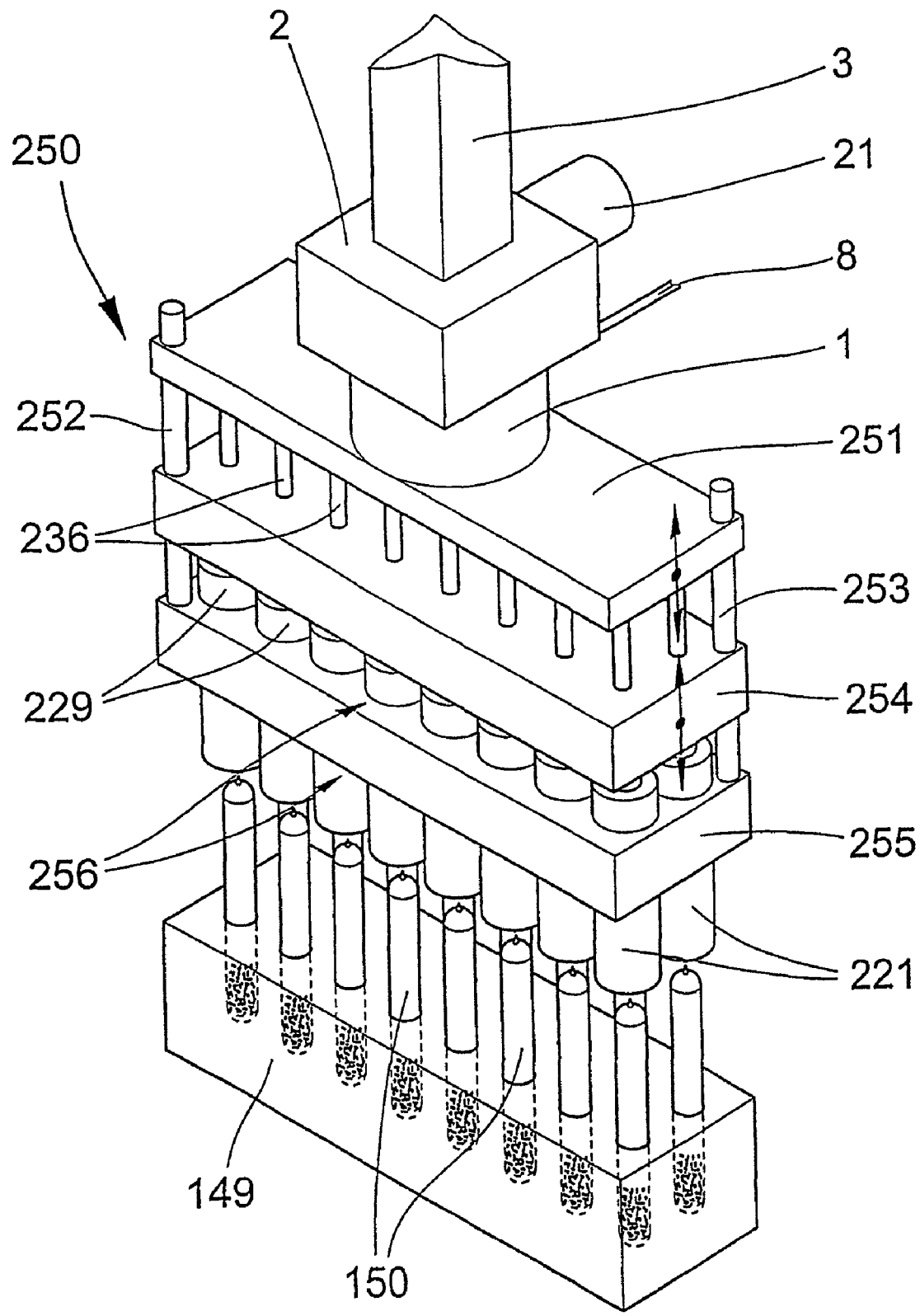
FIG. 15 shows the tool holder from FIG. 1 with a diagrammatically depicted matrix-capsule-handling head as tool and capsules arranged in a matrix.

To pick up a capsule 150, the capsule-transporting head 140 is moved such that the capsule-holding end piece 144 is above the top end of the capsule 150, and then the capsule 150 is picked up as a result of a reduced pressure being generated in the suction tube 143, as illustrated in FIG. 6. Then, the capsule 150 is transported by the linear axis system to the intended location, in FIG. 7 a reaction vessel 171 arranged in a matrix 170, where it is released into the reaction vessel 171 as a result of the reduced pressure in the suction tube 143 being eliminated.

FIG. 8

The tool is in this case formed by a matrix-capsule-transporting head 160 which comprises a permanent magnet 161, by means of which, as has been described in a corresponding way in connection with FIG. 2, it is connected to the tool holder 1. It is released by means of the electromagnet arranged in the tool holder 1. Sixteen suction tubes 163, which are arranged in the form of a matrix and each have a capsule-holding end piece 164, are attached to the permanent magnet 161 via a suction-tube plate 162. A reduced pressure can be generated in the suction tubes 163 via the suction-tube plate 162 by means of a conventional suction means (not shown).

To pick up capsules 150, the matrix-capsule-transporting head 160 is moved such that the capsule-holding end pieces 164 are above the top ends of the capsules 150, and then the capsules 150 are picked up as a result of a reduced pressure being generated in the suction tubes 163. Then, the capsules 150 are transported by the linear axis system to the intended location, in this case reaction vessels 171 arranged in a matrix 170, where the capsules 150 are dispensed into the reaction vessels 171 as a result of the reduced pressure in the suction tubes 163 being eliminated.

FIG. 9

In this case, a gripper 180 is secured as tool to the tool holder 1 by means of a permanent magnet 181. Once again, the gripper 180 is released from the tool holder 1 by means of the electromagnet arranged in the tool holder 1. The gripper 180 comprises three gripper arms 182 which can be pivoted away from the permanent magnet 181 in the direction of the arrows illustrated. The pivoting drive is arranged inside the permanent magnet 181.

Similar grippers 180 of this type which, however, are fixedly connected to the tool holder 1 are already known from the prior art. They can be used, for example, to grip and transport solids.

FIG. 10

In this case, the tool is formed by a lid opener 200, which comprises a permanent magnet 201, by means of which, as has been described in a corresponding way in connection with FIG. 2, it is connected to the tool holder 1. The lid opener 200 is released from the tool holder 1 by means of the electromagnet arranged in the tool holder 1.

On the one side, a motor 202, which opens and closes, under computer control, a clamp 203 having two clamping arms 204 and 205 in the directions indicated by arrows A and B, is secured to the permanent magnet 201. The clamp 203 engages around and holds a starting-material vessel 210 which is closed off by a lid 211.

On the other side, a strap 206, to the free end of which a cap-like lid-gripping element 207 is rotatedly attached, and which can be folded up as indicated by arrow C, is articulatedly mounted on the permanent magnet 201. The lid-gripping element 207 surrounds the lid 211 of the starting-material vessel 210 and is frictionally connected thereto. As an alternative, a positively locking connection would also be conceivable. To rotate the lid-gripping element 207 in the direction indicated by arrow D, a rotary motor 208 is attached to the strap 206. Actuation of the rotary motor 208 causes the lid-gripping element 207 to be rotated, rotating the lid 211 with it via the frictional connection, with the result that the lid is detached from the starting-material vessel 210. The strap 206 can then be folded up in the direction indicated by arrow C together with the lid-gripping element 207 and the lid 211.

FIG. 11 to 14

In this case, the tool is formed by a capsule-handling head 220, which comprises a cylindrical housing 221 which is divided into two compartments 223 and 224 by a partition 222 and is closed off at the top by an end wall 227. At the open end of the bottom compartment 223, in the cylindrical housing 221, there is an air-filled sleeve 225, for example made from rubber, which in the unladen state as shown in FIG. 11 has an internal diameter $d_{min}$. In the upper compartment 224 there is a plunger 226, to which a plunger rod 228, which projects out through the end wall 227 and is provided at its top end with an outer push-button 229, is attached. Between the plunger 226 and the cylindrical housing 221 and between the plunger rod 228 and the end wall 227 there is in each case an annular seal 230, 231. Between the plunger 226 and the partition 222 there is a coil spring 232, which in the unladen state holds the plunger 226 in the position shown in FIG. 11. Between the plunger 226 and the end wall 227 there is an air-filled space 233, which is in communication with the interior of the sleeve 225 via an air line 234.

In addition, the capsule-handling head 220 comprises a hollow needle 235, to which an inner push-button 236 is attached. The inner push-button 236 is mounted movably in a recess 237 in the outer push-button 229, a coil spring 238 being arranged in the recess 237 below the inner push-button 236, which coil spring 238, in the unladen state, holds the inner push-button 236 and the hollow needle 235 in the position shown in FIG. 11. The hollow needle 235 passes through the plunger rod 228, the plunger 226 and the partition 222. It is in communication with the internally hollow inner push-button 236, which can be fed, for example, with a solvent or another liquid via a feed line 239.

FIG. 12 shows the capsule-handling head 220 after it has picked up a capsule 150, an operation which can be effected by placing the capsule-handling head 220 onto the capsule 150. The capsule 150 is held by the sleeve 225, which now has an internal diameter d which corresponds to the external diameter of the capsule 150 and is greater than the internal diameter $d_{min}$ in the stress-free state.

FIG. 12 also illustrates that the capsule-handling head 220 comprises a permanent magnet 240, via which, as described in a corresponding way in connection with FIG. 2, it is connected to the tool holder 1. The capsule-handling head 220 is detached from the tool holder 1 by means of the electromagnet arranged in the tool holder 1. Moreover, the figure diagrammatically indicates that the inner push-button 236 can be actuated by a rotary lever 242 and the outer pushbutton 229 can be actuated by a rotary lever 244, the two rotary levers 242, 244 being articulatedly mounted on a rod. 243, which is secured to the permanent magnet 240, in such a manner that they can rotate in the direction indicated by the arrows. The drives for the two rotary levers 242, 244, which are controlled by the control computer, are not shown. FIG. 11, 13 and 14 do not show the permanent magnet 240, the two rotary levers 242, 244, the rod 243, and the tool holder 1, for reasons of clarity.

The coil spring 238 is compressed as a result of the inner push-button 236 being pushed downward, and as a result the hollow needle 235 is forced into the capsule 150, as illustrated in FIG. 13. As a result, the capsule 150 is opened and it can be supplied, via the hollow needle 235, with a substance from the inner push-button 236, which is fed via the feed line 239. Alternatively, the feed line 239 could also be connected directly to the hollow needle 235. The substance supplied, in this case a solvent, can be mixed with the substance which is already present in the capsule 150, for example by the capsule-handling head 220 being shaken. If a sufficiently long hollow needle is used, the mixing could also be effected by the substances which are present in the capsule 150 being sucked up and discharged again a number of times.

If pressure is no longer being exerted on the inner push-button 236, the coil spring 238 forces it back upward into the starting position.

In order for the capsule 150 to be released, the outer push-button 229 is pressed downward, as illustrated in FIG. 14. In the process, the plunger rod 228 and the plunger 226 are moved downward so as to compress the coil spring 232, with the result that the size of the space 233 between the plunger 226 and the end wall 227 is increased greatly and a reduced pressure is generated therein. This reduced pressure causes air to be extracted from the interior of the sleeve 225 via the air line 234, with the result that the internal diameter of the sleeve 225 is increased to a maximum value $d_{max}$, which is greater than the external diameter of the capsule 150, so that the capsule 150 is no longer held by the sleeve 225 and drops downward under the force of gravity.

If pressure is no longer being exerted on the outer pushbutton 239, the coil spring 232 forces it back upward into the starting position shown in FIG. 11.

FIG. 15

The tool is in this case formed by a matrix-capsule-handling head 250, which comprises a holding plate 255 which is removably connected to the tool holder 1 by means of a permanent magnet, in a manner which is not illustrated. The matrix-capsule-handling head 250 is detached from the tool holder 1 by means of the electromagnet which is arranged in the tool holder 1 and the power supply line 8 of which can be seen. Two rods 252, 253, which are fixedly connected to the holding plate 255, extend upward in the z direction, i.e. vertically, from two diagonally opposite corner regions of the holding plate 255. A release plate 254, which can be displaced in the z direction and is guided by the rods 252, 253 in two diagonally opposite corner regions, is arranged above the holding plate 255. A trigger plate 251 located above the release plate 254 can likewise be displaced in the z direction and is guided by the two rods 252, 253. The vertical displacement of the release plate 254 and of the trigger plate 251 is effected by two motors (not shown), although in principle it could also be brought about manually.

Sixteen capsule-handling elements 256 are secured in the holding plate 255. The capsule-handling elements 256, which are only diagrammatically depicted in this figure, apart from the connecting part 241 and the permanent magnet 240, are constructed in substantially the same way as the capsule-handling heads 220 shown in FIG. 11 to 14 and each comprise, in addition to a cylindrical housing 221, an outer push-button 229 and an inner push-button 236. The inner push-buttons 236 with the hollow needles attached to them can be actuated jointly as a result of the trigger plate 251 being lowered. The joint actuation of the outer pushbuttons 229 is effected as a result of the release plate 254 being lowered. The matrix-capsule-handling head 250 can be used to take hold of sixteen capsules 150 arranged in a matrix 149 together, to open each of them by means of a hollow needle 235 and if appropriate to mix the substances contained therein with other substances and release them again.

FIG. 16

The tool is in this case a first exemplary embodiment of a capsule-dispensing head 280, which comprises a permanent magnet 295, by means of which, as has been described in a corresponding way in connection with FIG. 2, it is connected to the tool holder 1. The removal of the capsule-dispensing head 280 from the tool holder 1 is effected by means of the electromagnet arranged in the tool holder 1.

The capsule-dispensing head 280 comprises a substantially cylindrical housing 281, the lower part of which narrows to form a neck 282 and in which a large number of capsules 150, which each contain a substance 151, are stored. One of the capsules 150 is held by an air-filled sleeve 283, which is arranged in the neck 282 and is made, for example, from rubber. In a separate cylinder 284 there is a plunger 285, to which a plunger rod 286, which projects out through an end wall 287 of the cylinder 284 and is provided at its top end with a push-button 288, is attached. Between the plunger 285 and the cylinder 284 and between the plunger rod 286 and the end wall 287 there is in each case an annular seal 289, 290. Between the plunger 285 and the base 291 of the cylinder 284 there is a coil spring 292, which in the stress-free state holds the plunger 285 in the position illustrated. Between the plunger 285 and the end wall 287 there is an air-filled space 293, which is in communication with the interior of the sleeve 283 via an air line 294.

In order for the capsule 150 which is being held by the sleeve 283 to be released, the push-button 288 is pressed downward. In the process, the plunger rod 286 and the plunger 285 are moved downward so as to compress the coil spring 292, with the result that the size of the space 293 between the plunger 285 and the end wall 287 is increased greatly and a reduced pressure is generated therein. This reduced pressure causes air to be extracted from the interior of the sleeve 283 via the air line 294, with the result that the internal diameter of the sleeve 283 is increased to a value which is greater than the external diameter of the capsule 150, so that the capsule 150 is no longer held by the sleeve 283 and drops downward under the force of gravity. At the same time, a second capsule 150 moves up to take the place of the first capsule 150, it being important for the pressure on the push-button 288 to be released again sufficiently quickly, so that the coil spring 292 moves the plunger 285 back upward into the starting position, the size of the space 293 is reduced again and air is fed back to the sleeve 283 via the air line 294 sufficiently quickly for the capsule 150 to be gripped by the sleeve 283.

Moreover, the figure diagrammatically indicates that the push-button 288 can be actuated by a rotary lever 297, the rotary lever 297 being articulatedly mounted on a rod 296 in such a manner that it can rotate in the direction of the arrow, this rod being secured to the permanent magnet 295. The drive of the rotary lever 297, which is controlled by the control computer, is not illustrated.

FIG. 17

The tool is in this case a second exemplary embodiment of a capsule-dispensing head 300, which comprises a permanent magnet 317, by means of which, as has been described in a corresponding way in connection with FIG. 2, it is connected to the tool holder 1. The removal of the capsule-dispensing head 300 from the tool holder 1 is effected by means of the electromagnet arranged in the tool holder 1.

The capsule-dispensing head 300 comprises a substantially cylindrical housing 301, which in its lower part narrows to form a neck 302 and in which a multiplicity of capsules 150, which each contain a substance 151, are stored. One of the capsules 150 is held by an air-filled sleeve 303, which is arranged in the neck 302 and is made, for example, from rubber, while the other capsules 150 are arranged in the cylindrical housing 301 in a chamber part 315 which can rotate in the manner of a revolver as indicated by arrow E. In a separate cylinder 304 there is a plunger 305, to which a plunger rod 306, which projects out through an end wall 307 of the cylinder 304 and is provided at its top end with a push-button 308, is attached. Between the plunger 305 and the cylinder 304 and between the plunger rod 306 and the end wall 307 there is in each case an annular seal 309, 310. Between the plunger 305 and the base 311 of the cylinder 304 there is a coil spring 312, which in the stress-free state holds the plunger 305 in the position illustrated. Between the plunger 305 and the end wall 307 there is an air-filled space 313, which is in communication with the interior of the sleeve 303 via an air line 314.

In addition, the capsule-dispensing head 300 comprises a hollow needle 316, which passes through the pushbutton 308, the plunger rod 306, the plunger 305 and the base 311. As a result of the hollow needle 316 being forced downward, the capsule 150 which is located above the capsule which is held by the sleeve 303 can be punctured. If necessary, another substance, in particular a solvent, can be fed to the open capsule 150 via the hollow needle 316.

In order for the capsule 150 which is being held by the sleeve 303 to be released, the push-button 308 is pushed downward. In the process, the plunger rod 306 and the plunger 305 are moved downward so as to compress the coil spring 312, with the result that the size of the space 313 between the plunger 305 and the end wall 307 is increased greatly and a reduced pressure is generated therein. This reduced pressure causes air to be extracted from the interior of the sleeve 303 via the air line 314, with the result that the internal diameter of the sleeve 303 is increased to a value which is greater than the external diameter of the capsule 150, so that the capsule 150 is no longer held by the sleeve 303 and drops downward under the force of gravity. At the same time, the capsule located above this capsule 150 drops into the position which was occupied by the capsule 150 which has been released, it being important for the pressure on the push-button 308 to be released again sufficiently quickly, so that the coil spring 312 moves the plunger 305 back upward into the starting position, the size of the space 313 is reduced again and air is fed back to the sleeve 303 via the air line 314 sufficiently quickly for the next capsule 150 to be gripped by the sleeve 303. Then, the chamber part 315 is rotated one step onward, so that a new capsule 150 moves into the position directly above the neck 302. The rotation of the chamber part 315 may be effected externally, for example by hand, or may be triggered by the actuation of the push-button 308. For this purpose, if necessary, the cylindrical housing 301 has access openings.

Moreover, the figure diagrammatically indicates that the hollow needle 316 can be actuated by a rotary lever 319 and the push-button 308 can be actuated by a rotary lever 318, the two rotary levers 319, 318 being articulatedly mounted on a rod 321, which is secured to the permanent magnet 317, in such a manner that they can rotate in the direction indicated by the arrows. The drives of the two rotary levers 319, 318, which are controlled by the control computer, are not shown.

A cuboidal housing, in which the capsules 150 are arranged in a plate which can be moved in the x direction and in the y direction, may also be provided instead of the cylindrical housing 301 and the chamber part 315 which can rotate in the manner of a revolver.

Figure 19:
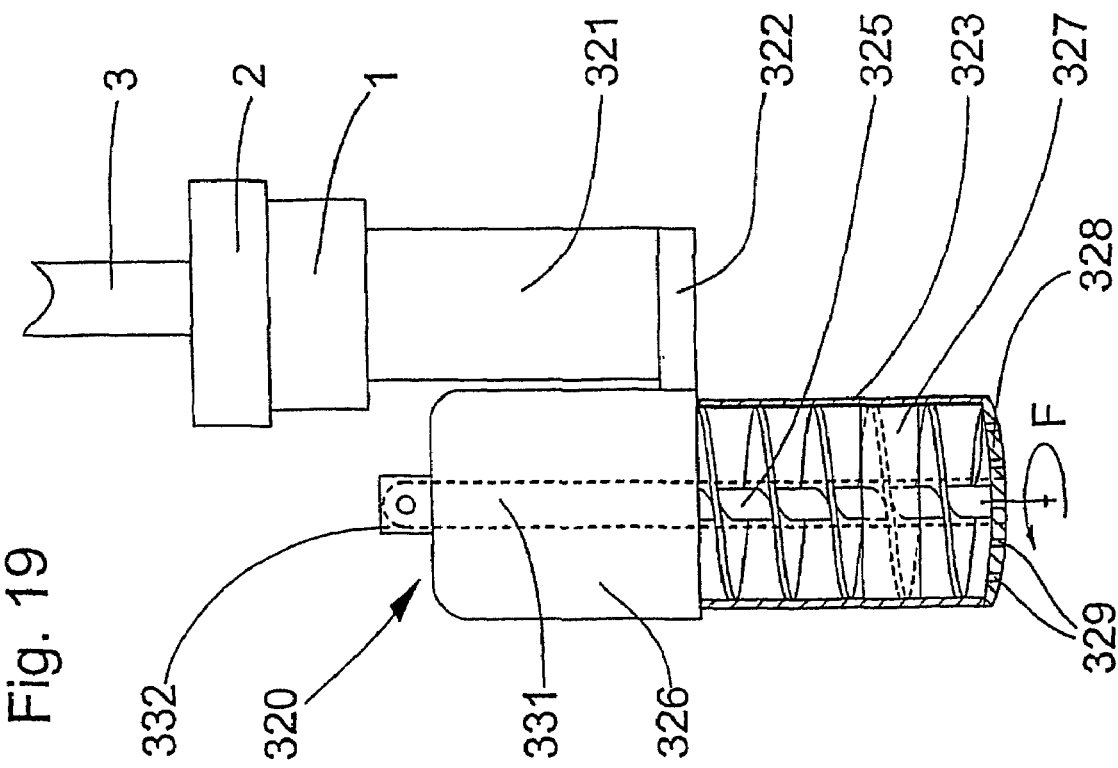
FIG. 19 shows the tool holder with screw metering head from FIG. 18 with a diaphragm which has been pivoted under the screw, in a partially sectional view.
Figure 18:
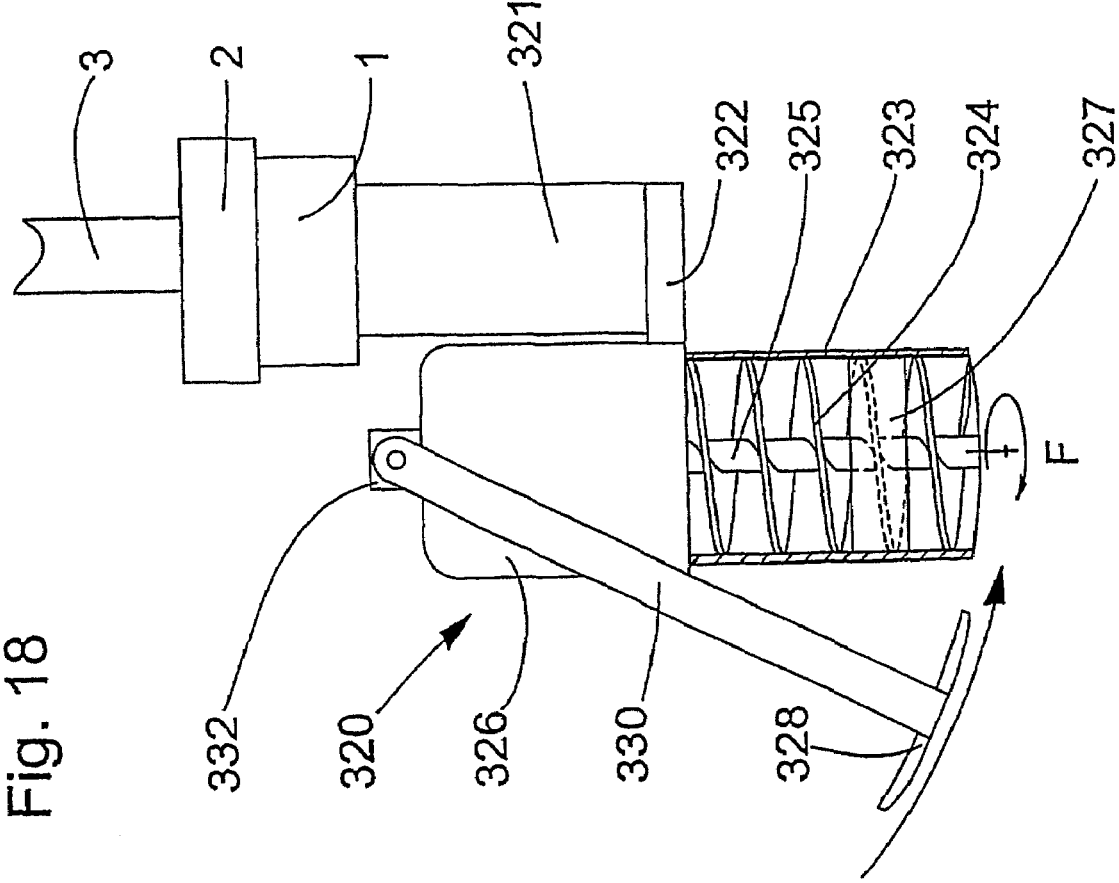
FIG. 18 shows the tool holder shown in FIG. 1 with a screw metering head as tool, with a diaphragm which has been pivoted away, in a partially sectional illustration.
Figure 20:
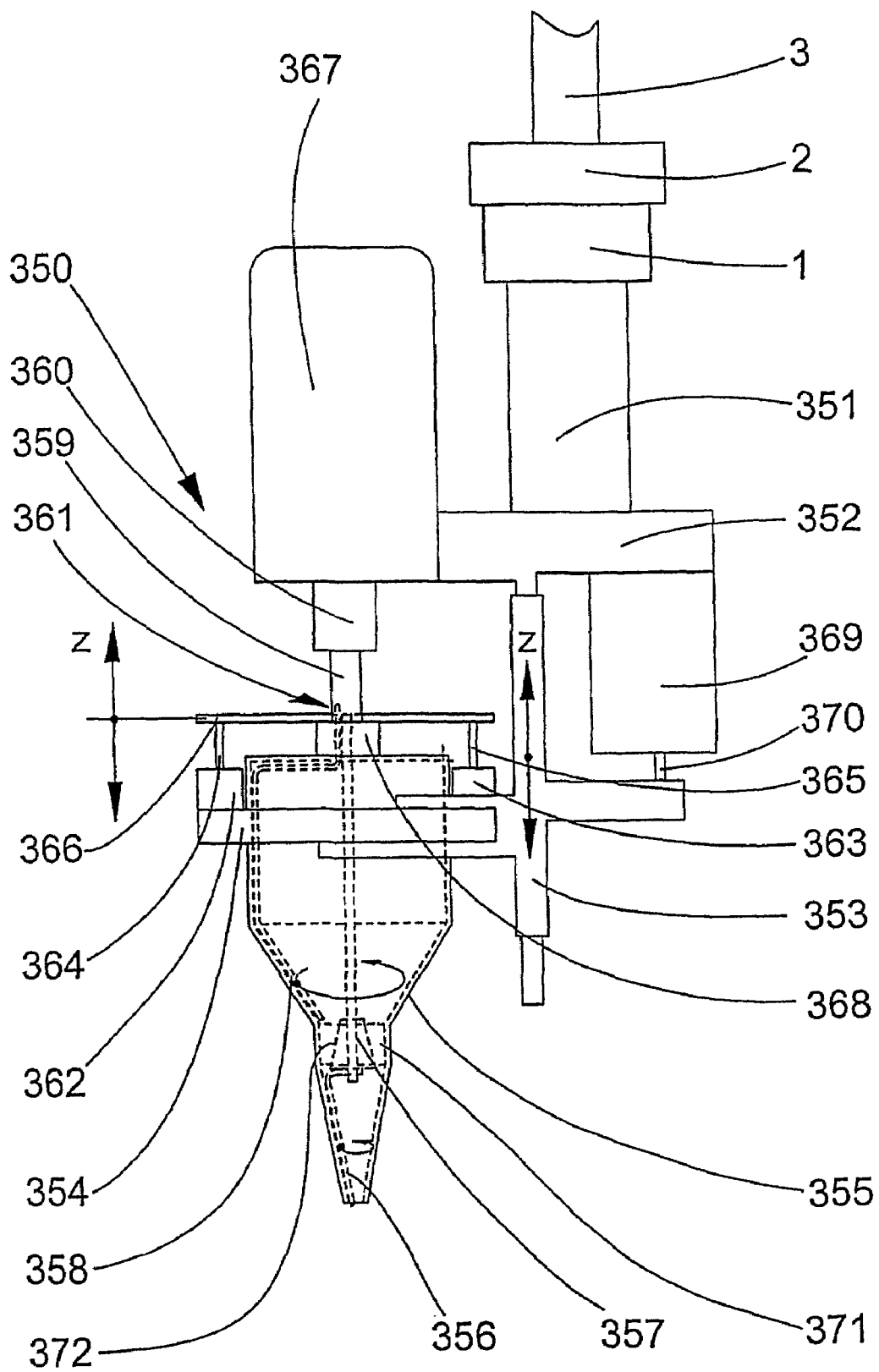
FIG. 20 shows the tool holder from FIG. 1 with a solids-metering head as tool.

FIGS. 18 and 19

The tool is in this case formed by a screw metering head 320, which comprises a permanent magnet 321, by means of which, as has been described in a corresponding way in connection with FIG. 2, it is connected to the tool holder 1. The removal of the screw metering head 320 from the tool holder 1 is effected by means of the electromagnet arranged in the tool holder 1.

A motor part 326 is attached to the permanent magnet 321 by means of a connecting part 322, and an open tube 323, in which a screw 324, which can rotate forward and backward about the z direction as indicated by arrow F, with screw shaft 325 is mounted, is secured to its bottom end. The screw 324 can be rotated via the screw shaft 325 by a motor arranged in the motor part 326 and is stably anchored in the z direction. Rotation of the screw 324 results in a ram 327 which runs on the screw moving up or down. The lower, open end of the tube 323 can be closed off by means of a diaphragm 328 which is provided with holes 329 and is secured to two pivot arms 330, 331 which are mounted pivotably in a suspension 332 on the motor part 326. In FIG. 18, the diaphragm 328 has been removed from the open end of the tube 323 and can be moved into the closed position illustrated in FIG. 19 by being pivoted in the direction of the arrow.

To take up substance, the open end of the tube 323 is moved onto the substance with the diaphragm 328 in its pivoted-away position. Rotation of the screw 324 in the direction which moves the ram 327 upward causes substance to be carried upward directly by the screw 324.

To dispense substance, the diaphragm 328 is pivoted under the screw 324 to cover the open end of the tube 323. Then, the screw 324 is rotated in the direction which moves the ram 327 downward, with the result that substance is forced out downward through the holes 329 in the diaphragm 328 on the one hand directly by the screw 324 and on the other hand by means of the ram 327.

The diaphragm 328 is responsible for continuous delivery of substance, but in principle metering is also possible without a diaphragm 328.

FIG. 20

The tool is in this case formed by a solids-metering head 350, which comprises a permanent magnet 351, by means of which, as has been described correspondingly in connection with FIG. 2, it is connected to the tool holder 1. The removal of the solids-metering head 350 from the tool holder 1 is effected by means of the electromagnet arranged in the tool holder 1.

On the permanent magnet 351 there is a bearing part 352, on which a carriage 353 is mounted in such a manner that it can move in the z direction. A holding plate 354 has been pushed laterally into the carriage 353 and has attached to it a metering housing 355, the internal diameter of which decreases in steps toward the bottom and which has an intermediate base 371 with a conical metering opening which tapers upward. The holding plate 354 with the metering housing 355 can be detached from the carriage 353 by means of a horizontal movement involving little force.

A rotating metering shaft 357, which drives a stripper 356 and can be displaced in the z direction, runs in the z direction centrally through the metering housing 355 and the conical metering opening in the intermediate base 371. At the lower end of the metering shaft 357 there is a closure cone 372 which tapers upward and partially or completely closes off the conical metering opening in the intermediate base 371 depending on the z position, substance which flows downward when the metering opening is partially open being fed to the stripper 356.

The rotating metering shaft 357 is fixedly connected to a co-rotating bearing part 368, projects from below into a shaft 359 driven by a motor 360 and is rotated with the shaft 359. A rotating stripper 358 which is arranged in the upper part of the metering housing 355 runs through the bearing part 368 and likewise projects into the shaft 359 from below. The stripper 358 can move in the z direction in the bearing part 368 and is driven, together with the metering shaft 357, by the shaft 359.

The displacement of the metering shaft 357 in the z direction is brought about by two electromagnets 362 and 363, which are mounted on the holding plate 354 and bear a cover plate 366 via two support parts 364, 365. The cover plate 366 is connected to the bearing part 368 fixedly in the z direction, a ball bearing 361 enabling the bearing part 368 to rotate on the rotationally fixed cover plate 366. On activation, the electromagnets 362, 363 generate a force in the z direction and raise or lower the cover plate 366 and as a result the bearing part 368 and the metering shaft 357.

The motor 360 and the electromagnets 362, 363 are controlled by a control part 367, which is arranged laterally on the bearing part 352 and to which the motor 360 is secured.

Moreover, a balance 369 with a minimum weighing range from 0 to 2 kg and an accuracy of 0.1 g, which is in contact with the carriage 353 via a pin 370, is attached to the bearing part 352. Balances of this type are commercially available, for example from Sartorius AG, 37070 Gottingen, Germany.

If substance which is stored in the metering housing 355 is dispensed via the conical metering opening in the intermediate base 371, the weight load applied to the carriage 353 is reduced and the carriage 353 is pulled downward less strongly, a fact which is measured by the balance 369 via the pin 370.

A solids-metering head of this type, but without magnet coupling to the tool holder 1 and without balance 369 arranged directly on the solids-metering head, is marketed by Auto Dose SA, CH-1228 Plan-les-Ouates.

It is possible to execute further design variations on the devices according to the invention which have been described above. Express mention should also be made of the following at this point:

The other tools, like the solids-metering head 350, may also be provided with a balance 369. As an alternative, it is also conceivable for the balance to be attached to the tool holder 1.

The connection between tool holder 1 and tool may also be formed in a different way than with magnets. By way of example, screw connections, bayonet catch connections or clamping connections are conceivable. However, it should be possible for the connection to be produced and released again automatically, i.e. not by hand.

In addition to the tools described, it is also possible to use further tools which are equipped with a connection point to the tool holder. By way of example, the camera 10 or the infrared-analysis unit could also be designed as independent tools.

What is claimed is:

1. A device for use with two or more reaction vessels, the device comprising:
   a tool holder, which can be displaced in an x direction and a z direction which is perpendicular to the x direction;
   a first tool in the form of at least two dispensers, that are individually displaceable in the z direction by first motive means of the first tool, the distance between the at least two dispensers can be adjusted by a further motive means of the first tool, and that, when the device is used in combination with two or more of the reaction vessels, are spaced away from each other a distance that is generally equal to a distance that separates the at least two reaction vessels;
   at least one further tool that is adapted to be removably secured to the tool holder as an alternative to the first tool, and
   a controller, the first and at least one further tool being arranged with respect to the controller so that the controller can automatically cause the first tool to be removed from the tool holder and thereafter automatically cause the at least one further tool to be removably secured to the tool holder, the automatic changeover from the first tool to the at least one further tool allowing for (i) the performance or preparation of a chemical reaction in a reaction vessel or (ii) the mixture of chemicals.

2. The device as claimed in claim 1, wherein the tool holder can rotate about the z direction relative to the x direction.

3. The device as claimed in claim 1, wherein the tool holder can be displaced in a y direction which is perpendicular to the x direction and to the z direction.

4. The device as claimed in claim 1, wherein the tools are secured to the tool holder by means of magnets.

5. The device as claimed in claim 1, wherein the dispensers comprise needles.

6. A combination comprising the device as claimed in claim 1 and two or more reaction vessels.

7. A device, comprising:
   a tool holder, which can be displaced in an x direction and a z direction which is perpendicular to the x direction;
   a first tool in the form of a multi-needle head with a plurality of hollow needles, which are individually displaceable in the z direction by first motive means of the first tool and the distance between which can be adjusted by a further motive means of the first tool, wherein the first tool can be removably secured to the tool holder; and
   at least one further tool, which can be removably secured to the tool holder as an alternative to the first tool, wherein securing and removal of the first tool and/or the further tool can be carried out automatically.

8. The device as claimed in claim 7, wherein the tool holder can rotate about the z direction relative to the x direction.

9. The device as claimed in claim 7, wherein the tool holder can be displaced in a y direction which is perpendicular to the x direction and to the z direction.

10. The device as claimed in claim 7, wherein the tools are secured to the tool holder by means of magnets.

11. A combination comprising the device as claimed in claim 7 and two or more reaction vessels.

* * * * *